(12) United States Patent
Cheng et al.

(10) Patent No.: US 8,808,518 B2
(45) Date of Patent: Aug. 19, 2014

(54) MICROBIAL IDENTIFICATION AND MANIPULATION OF NANOSCALE BIOMOLECULES

(75) Inventors: I-Fang Cheng, Tainan (TW); Hsien-Chang Chang, Tainan (TW); Cheng-Che Chung, Hualien County (TW)

(73) Assignee: National Cheng Kung University, Tainan (TW)

( * ) Notice: Subject to any disclaimer, the term of this patent is extended or adjusted under 35 U.S.C. 154(b) by 185 days.

(21) Appl. No.: 13/108,216

(22) Filed: May 16, 2011

(65) Prior Publication Data
US 2012/0292184 A1 Nov. 22, 2012

(51) Int. Cl.
| | |
|---|---|
| B01D 57/02 | (2006.01) |
| G01N 33/536 | (2006.01) |
| G01N 33/58 | (2006.01) |
| B03C 5/02 | (2006.01) |
| G01N 33/569 | (2006.01) |
| G01N 33/558 | (2006.01) |
| C12N 13/00 | (2006.01) |
| C12Q 1/68 | (2006.01) |
| B03C 5/00 | (2006.01) |

(52) U.S. Cl.
CPC ............ *C12Q 1/6816* (2013.01); *G01N 33/536* (2013.01); *G01N 33/582* (2013.01); *B03C 5/026* (2013.01); *G01N 33/569* (2013.01); *G01N 33/558* (2013.01); *G01N 33/583* (2013.01); *C12N 13/00* (2013.01); *B03C 5/005* (2013.01)
USPC ............................. 204/547; 204/643; 204/400

(58) Field of Classification Search
USPC .................. 204/766, 550, 450, 547, 600, 643; 435/6, 287.2
See application file for complete search history.

(56) References Cited

U.S. PATENT DOCUMENTS

2009/0092989 A1* 4/2009 Chang et al. ...................... 435/6

OTHER PUBLICATIONS

Cheng et al., A rapid field-use assay for mismatch number and location of hybridized DNAs, Lab Chip, 2010, 10, 828-831.*
Chen et al., A continuous high-throughput bioparticle sorter based on 3D traveling-wave dielectrophoresis, Lab on Chip, 2009, 9, 3193-3201.*

\* cited by examiner

*Primary Examiner* — Luan Van
*Assistant Examiner* — Gurpreet Kaur
(74) *Attorney, Agent, or Firm* — Muncy, Geissler, Olds & Lowe, P.C.

(57) ABSTRACT

A method of microbial identification is disclosed. The method includes the steps of assembling dielectrophoretic particles modified with specific DNA probes on a surface thereof in a continuous fluid at a predetermined location in a microchannel to form a particle assembly by a negative dielectrophoretic force and a hydrodynamic force provided by the continuous fluid, narrowing gaps between the dielectrophoretic particles of the particle assembly to enhance the electric field in the gaps between the dielectrophoretic particles, injecting a fluid containing target DNAs of a target microbe into the microchannel at a predetermined flow rate to move the target DNAs toward the particle assembly and generating a positive dielectrophoretic force by the enhanced electric field to attract the target DNAs toward the dielectrophoretic particles of the particle assembly for hybridization with the DNA probes. The present invention also discloses a method of manipulation of nanoscale biomolecules.

11 Claims, 12 Drawing Sheets

(a)

(b)

(c)

MICROBIAL IDENTIFICATION AND MANIPULATION OF NANOSCALE BIOMOLECULES

BACKGROUND OF THE INVENTION

1. Field of Invention

The present invention relates to a method of identification and a method of manipulation and, in particular, to a method of bio-identification and a method of manipulation of nanoscale biomolecules by dielectrophoresis.

2. Related Art

Clinically, *Candida albicans* and *Candida tropicalis*, which are two common species within *Candida*, can easily cause infection and disease in humans suffering from hypoimmunity, especially in AIDS patients, patients in ICU (instruction control unit), cancer patients receiving chemotherapy and organ transplant recipients suffering from hypoimmunity. The diseases caused by *Candida albicans* and *Candida tropicalis* should be treated as soon as possible after infection. Otherwise, it would lead to Fungemia, which is a complicated disease for treatment and with an extremely high fatality rate. The effectiveness of medication varies with the species of pathologic fungi. Administration with improper medication would lead to fairly poor treatment effect. Severely, improper administration or using common antibiotics frequently would also cause drug resistance of human body. That is, it results in antibiotic resistance in some strains, and, as a result, healing of the aforementioned infection would become very difficult. Hence, it is very crucial to precisely and rapidly detect and identify the species of the pathologic fungi for medication on fungi infection.

However, traditional approach for strain identification by visual inspection requires a long incubation period. For example, yeast has to be incubated for 24~72 hours, and fungi even have to be incubated for 1~2 weeks. It is obviously impractical and cannot meet clinical requirements. In recent years, strain identification with DNA-based technique has becoming a common trend in the field of rapid strain identification. However, while current novel DNA chips allow operators to identify multiple target sources simultaneously, it requires a high DNA concentration of the samples. For those samples containing low DNA concentration, it takes about 3~4 hours to perform 30~40 cycles of PCR to increase the DNA concentration up to 100 nM~1 M before hybridization assay. Furthermore, the conventional hybridization mechanism depends mainly on diffusion so that it takes about 3~4 hours to react. Briefly, it is inevitable to take about 6~8 hours for strain identification on the DNA chips.

In addition, identification on the DNA chips could be very inaccurate for some strains with sequences containing few base mismatches. It is mainly because the DNA chips require a hybridization solution (4×SSC buffer with a conductivity of 10 mS/cm) with a high ion concentration in operation. However, the high ion concentration in the solution reduces the electrostatic repulsive force between target DNAs and DNA probes so as to prevent DNA separation after hybridization. In other words, even though the target DNAs contain one- to three-base mismatch, they still can adhere tightly on the DNA probes. Therefore, during hybridization, it is usually considered to heat up the DNA chips to a predetermined temperature (about 45~55□) to increase the selectivity by thermo agitation mechanism in combination with DNA flushing to remove the DNAs containing few base mismatch. Unfortunately, the flushing step usually accidentally removes some hybridized target DNAs and thereby weakens the intensity of fluorescent signal and the sensitivity of the identification.

Another approach of microbial identification is immunoassay, for example ELISA. In general, the procedure of the immunoassay has to modify a substrate with antibodies first to trap specific proteins on the surface of a target first and fix the target on the surface of the substrate. Then, after adding secondary antibodies modified with fluorescent material or color display material to bind the specific proteins on the surface of the target, the identification result can be observed by the fluorescence intensity or color development. However, since two modifications and a period for fixing the target with the antibodies are required, the procedure generally takes approximately 10~12 hours to complete all the steps. It is relatively time-consuming and has low sensitivity.

Because a dielectrophoretic force has a major inverse relationship to the square of the diameter of a particle in fluid, it is very difficult to manipulate nanoscale small molecules such as DNAs, virus, antibodies and proteins by the dielectrophoretic force. Manipulation of nanoscale biomolecules, for example the coiled DNA with the size of about 1~10 nm, requires an electric field intensity higher than $10^8$ V/m. That is, it is essential to use nanoelectrodes with the size of 10~20 nm and a AC voltage of 10~20 $V_{pp}$ to generate the dielectrophoretic force considering not to inducing electrolysis at the electrodes. Such small-sized electrodes only can be manufactured in nanoprocess and, in particular, is very difficult to manufacture and low-yield. To this end, no dielectrophoretic microfluidic chip is qualified for manipulation of nanoscale small molecules such as DNAs, virus, antibodies and proteins currently.

SUMMARY OF THE INVENTION

Hence, the purpose of the present invention is to provide a rapid, highly sensitive and highly specific method of bio-identification.

Another purpose of the present invention is to provide a method of manipulation of nanoscale biomolecules by dielectrophoretic forces.

Accordingly, the method of biomolecule identification in accordance with the present invention includes the steps of assembling dielectrophoretic particles modified with specific DNA probes on a surface thereof in a continuous fluid at a predetermined region in a microchannel to form a particle assembly by a negative dielectrophoretic force and a hydrodynamic force provided by the continuous fluid, narrowing gaps between the dielectrophoretic particles of the particle assembly to enhance the electric field in the gaps between the dielectrophoretic particles, injecting a fluid containing target DNAs of a target microbe into the microchannel at a predetermined flow rate to move the target DNAs toward the particle assembly and generating a positive dielectrophoretic force by the enhanced electric field to attract the target DNAs toward the dielectrophoretic particles of the particle assembly for hybridization with the DNA probes, wherein the target DNAs are modified with fluorescent material or color display material Accordingly, the method of microbial identification in accordance with the present invention includes the steps of assembling target microbes in a continuous fluid at a predetermined region in a microchannel to form a particle assembly by a negative dielectrophoretic force and a hydrodynamic force provided by a continuous fluid, narrowing gaps between the target microbes of the particle assembly to enhance the electric field in the gaps between the target microbes, injecting a fluid containing specific antibodies into the microchannel at a predetermined flow rate to move the antibodies toward the particle assembly and generating a positive dielectrophoretic force by the enhanced electric field to attract the antibodies toward the microbes of the particle assembly in contact with the microbes for interaction, wherein the antibodies are modified with fluorescent material or color display material.

Accordingly, the method of manipulation of nanoscale biomolecules in accordance with the present invention includes the steps of assembling dielectrophoretic particles in a continuous fluid at a predetermined region in a microchannel to form a porous particle assembly by a negative dielectrophoretic force and a hydrodynamic force provided by the continuous fluid, narrowing gaps between the dielectrophoretic particles of the porous particle assembly to enhance the electric field in the gaps between the dielectrophoretic particles, injecting a fluid containing nanoscale biomolecules into the microchannel at a predetermined flow rate to move the nanoscale biomolecules toward the porous particle assembly and generating a positive dielectrophoretic force on the nanoscale biomolecules in the continuous fluid by the enhanced electric field in the gaps of the dielectrophoretic particles of the porous particle assembly.

The feature of the present invention is to assemble dielectrophoretic particles in a continuous fluid to form a particle assembly with nanogaps by a negative dielectrophoretic force and a hydrodynamic force provided by the continuous fluid. Hence, the high electric field intensity for generating the dielectrophoretic force to efficiently manipulate the nanoscale biomolecules can be directly formed in the nano gaps between the dielectrophoretic particles instead of being provided with nanosize trapping electrodes manufactured in nanoprocess. It breaks the bottleneck of the manipulation of nanoscale molecules by dielectrophoretic forces.

BRIEF DESCRIPTION OF THE DRAWINGS

The invention will become more fully understood from the detailed description and accompanying drawings, which are given for illustration only, and thus are not limitative of the present invention, and wherein.

DETAILED DESCRIPTION OF THE INVENTION

The present invention will be apparent from the following detailed description, which proceeds with reference to the accompanying drawings, wherein the same references relate to the same elements.

Figure 1:
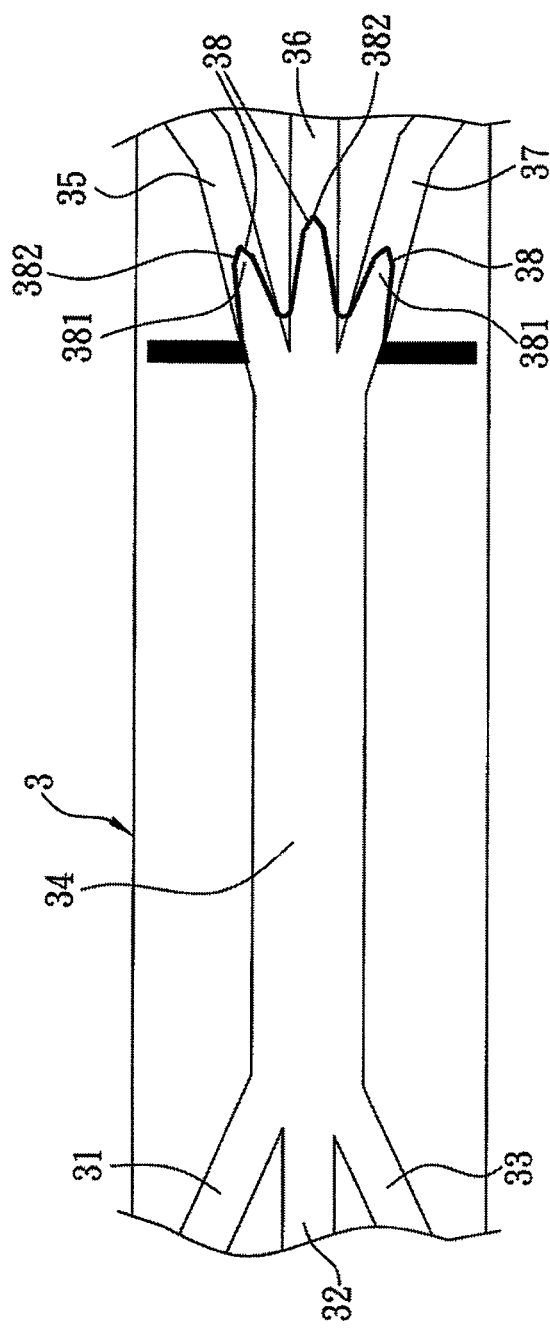
FIG. 1 is the top view schematically showing the dielectrophoretic microfluidic chip used in the present invention of bio-identification and is used to explain the relationship between the microchannels and the V-shaped trapping electrodes.

As shown in FIG. 1, a method of bio-identification in accordance with the first preferred embodiment of the present invention is used for rapidly identify species of microbes, virus or cells by DNA hybridization and fluorescent detection. In the present embodiment, the methods of microbial identification and cell identification are taken for exemplary description only. The entire identification process is operated on a dielectrophoretic microfluidic chip 3, including a first injection channel 31, a second injection channel 32 and a third injection channel 33, a main channel 34 extending horizontally and conduct to the injection channels 31~33 at left end thereof and a first microchannel 35, a second microchannel 36 and a third microchannel 37 conduct to the right end of the main channel 34 respectively. V-shaped trapping electrodes are separately disposed on the top side and the bottom side of each of the microchannel 35~37 with respect to each other. In the present embodiment, the width and height of the microchannels 35~37 are for example but not limited to 350 μm and 10 μm respectively.

The V-shaped openings 381 of the V-shaped trapping electrodes 38 disposed symmetrically on the top and bottom side face the main channel 34 toward the flow direction of a microfluid, and narrow ends 382 of the V-shaped trapping electrodes 38 points the flow direction of the microfluid. A predetermined frequency of AC voltage can be applied to the symmetrical V-shaped trapping electrodes 38 and generate a positive or a negative dielectrophoretic force on the dielectrophoretic particles (not shown in FIG.) in the microfluid in the microchannels 35~37. In the present embodiment, the wire diameter of the V-shaped trapping electrodes 38 is 30□m, and the included angle of the opening 381 of the narrow ends 382 is 90°. However, the configuration of the V-shaped trapping electrodes 35~37 is not limited to the aforementioned.

Dielectrophoresis (DEP) method is a technique to manipulate or separate biological or non-biological dielectrophoretic particles in accordance with the dielectrophoretic feature, size and shape of the dielectrophoretic particles. When a dielectrophoretic particle is present in an inhomogeneous electric field, it is polarized and induced by the electric field so as to form an induced dipole. Meanwhile, because a different degree of polarization exists between the dielectrophoretic particle and its surrounding fluid, the dielectrophoretic force is generated on the dielectrophoretic particle. When the degree of polarization of dielectrophoresis particles is higher then that of liquid, the positive dielectrophoresis (pDEP) force is generated and thereby attract the dielectrophoretic particles to move toward a region with a high electric field intensity. In contrast, if the polarizing ability of the dielectrophoretic particles is weaker than that of the surrounding fluid, the negative dielectrophoresis force is generated and thereby to repel the dielectrophoretic particles away from the region with a high electric field intensity. The basic technique of manipulating the dielectrophoretic particles by the dielectrophoretic force are well-known in the field of the present invention and thereby needs no further description.

Figure 2:
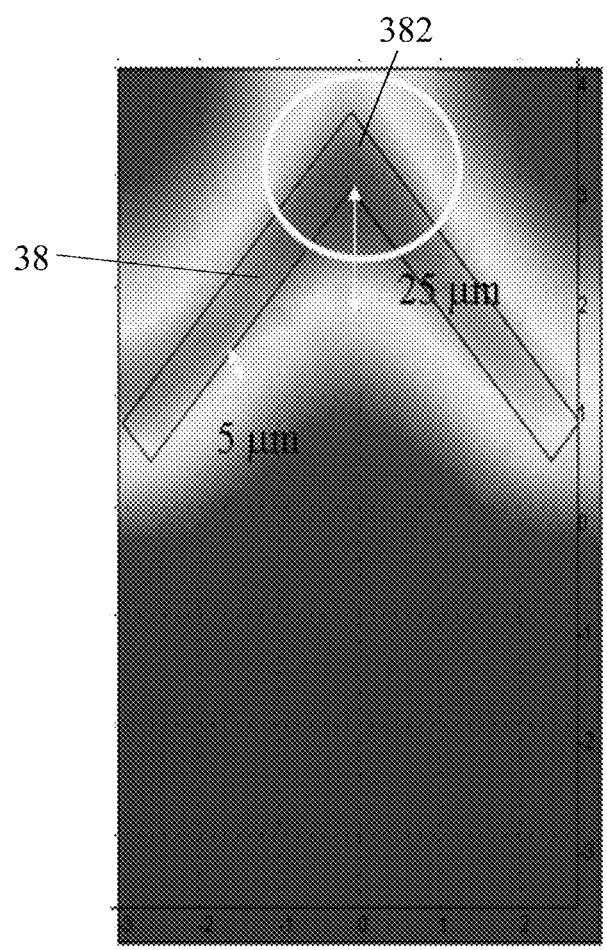
FIG. 2 shows the distribution of the electric fields when an AC with a predetermined frequency is applied to the V-shaped trapping electrodes in accordance with the first preferred embodiment.

Referring to FIG. 2, when the predetermined frequency of the AC voltage is applied to the V-shaped trapping electrodes 38 disposed symmetrically and separately on the top and bottom side, the dielectrophoretic field is formed in three-dimension between the V-shaped trapping electrodes 38. The intensity of the electric field between two V-shaped trapping electrodes 38 is higher than others and the region with the highest electric field intensity is at the narrow end 382 of the V-shaped trapping electrode 38.

If the negative dielectrophoretic force is generated on the dielectrophoretic particles, a dielectrophoretic wall is formed in the region between the V-shaped trapping electrodes 38 in the meantime. Then, the dielectrophoretic particles are repelled and blocked in front of the V-shaped trapping electrodes 38 by the high intensity of the electrical field between the V-shaped trapping electrodes 38. However, the dielectrophoretic particles are still moved forward by the continuous fluid and thereby gradually concentrated between the openings of the narrow ends 382, where the electric field lines gather. In accordance with certain feature, the present invention can assemble the dielectrophoretic particles to form a three dimensional particle assembly by controlling the flow rate of the continuous fluid to tightly compress the submicron dielectrophoretic particles blocked in front of the narrow ends 382 by the interaction of the hydrodynamic force and the negative dielectrophoretic force.

Figure 3:
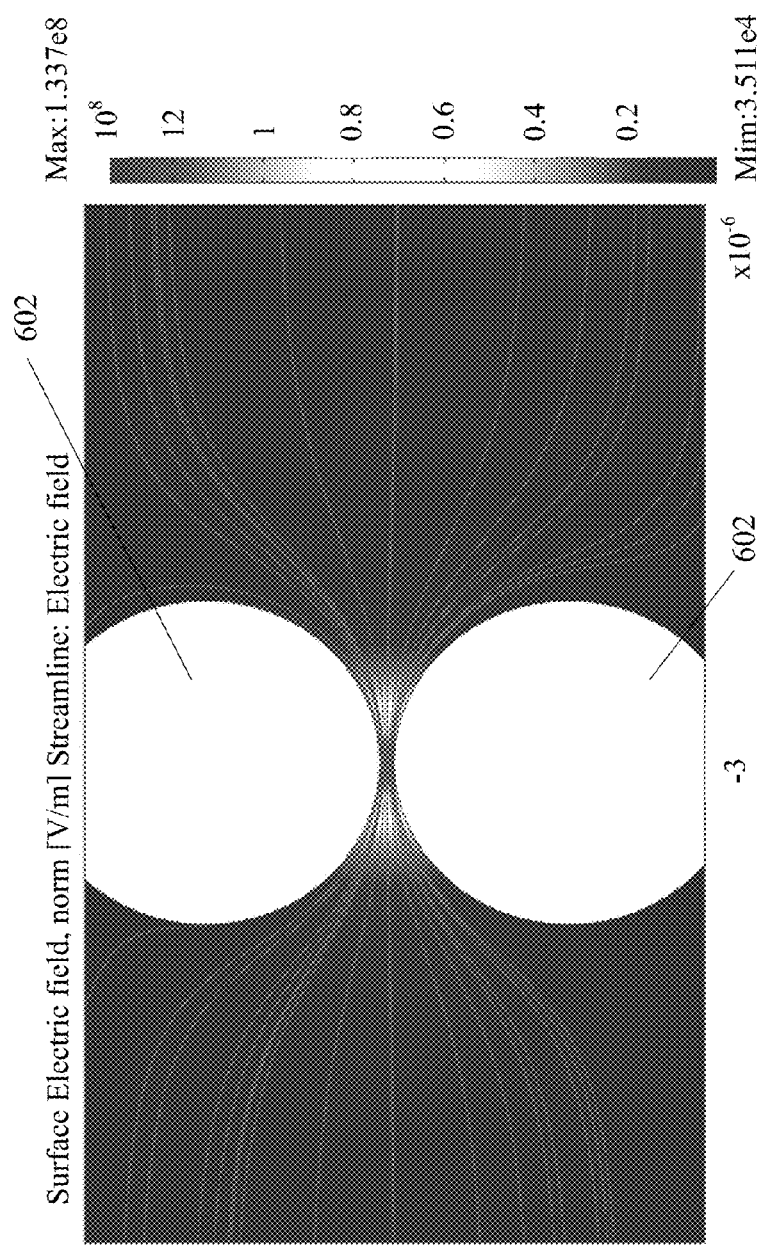
FIG. 3 shows the distribution of the electric field in the nano gaps between the dielectrophoretic particles when the electric field of the V-shaped trapping electrodes is enhanced between two dielectrophoretic particles in accordance with the first preferred embodiment.
Figure 4:
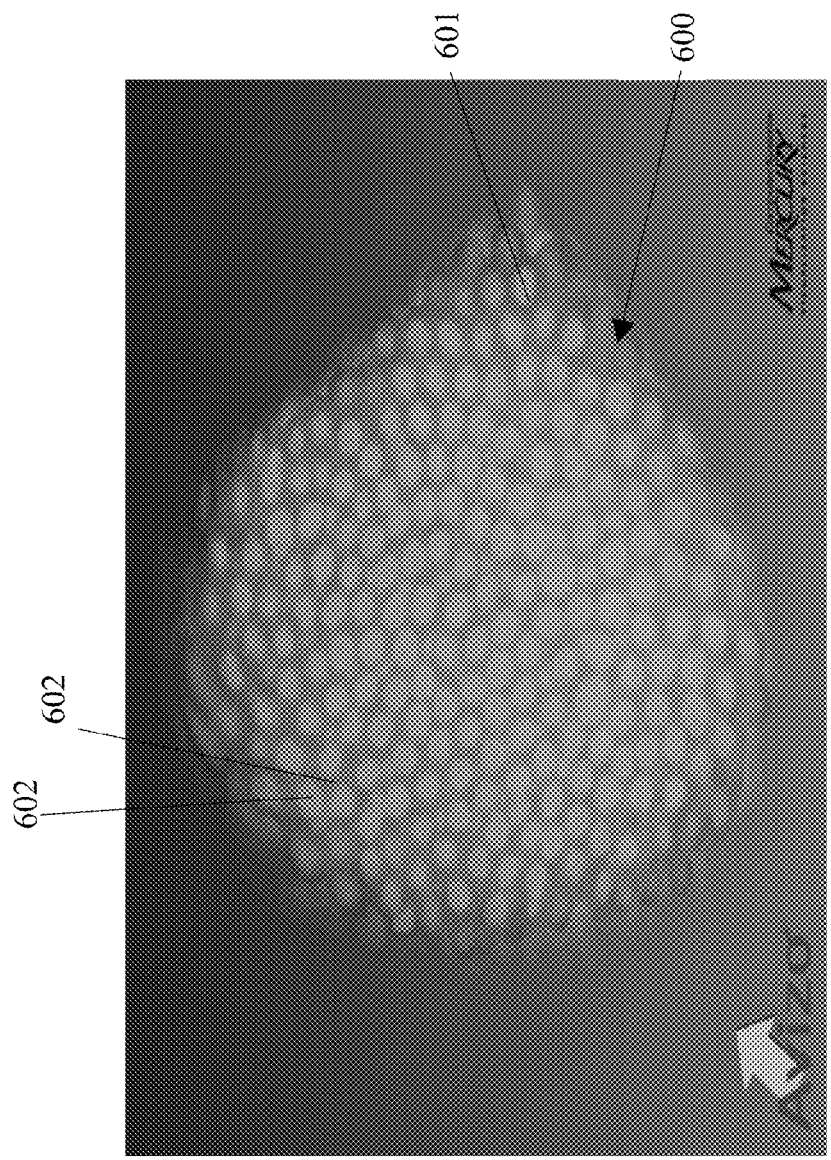
FIG. 4 is the confocal microscope image of the particle assembly in accordance with the first preferred embodiment.
Figure 7:
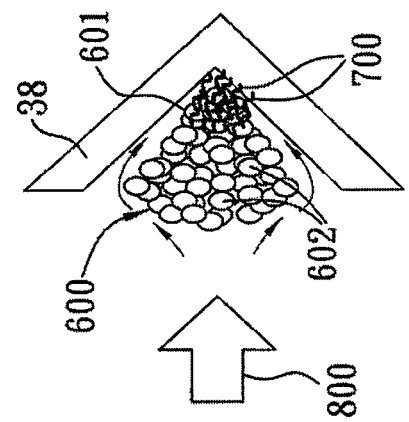
FIG. 7 is a similar figure of FIG. 5 showing the hybridization of the target DNAs occurring at the tip of the particle assembly.
Figure 6:
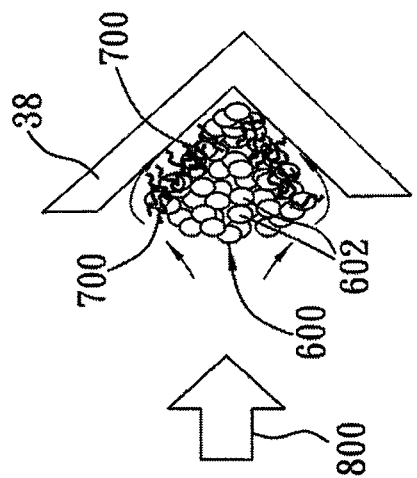
FIG. 6 is a similar figure of FIG. 5 showing the hybridization of the target DNAs occurring around the particle assembly.
Figure 5:
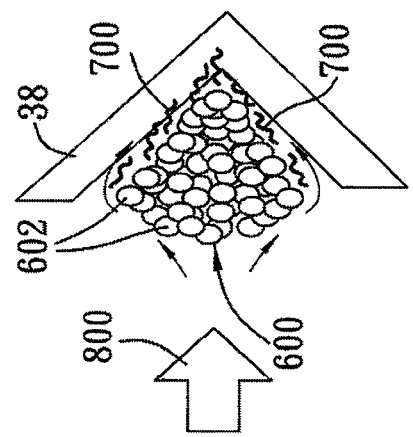
FIG. 5 is a schematic figure showing the target DNAs are repelled outside of the particle assembly when passing through the particle assembly in accordance with the first preferred embodiment.

Referring to FIGS. 3 and 4, the particle assembly 600 formed by dielectrophoretic particles 602 with a diameter of 500 nm is taken for exemplary description. Speculated from the confocal microscopic image, the size of the gaps between the dielectrophoretic particles 602 of the particle assembly 600 can be down to 10~20 nm. Additionally, since the trapping electrodes 38 is configured in a V-shape, the particle assembly 600 correspondingly has a tip 601 with an external diameter, which is gradually narrowing close to the narrow end 382 of the trapping electrode 38.

In accordance with the feature of assembling the particle assembly 600 by the dielectrophoretic particles 602, the present invention makes certain spaces filled with dielectrophoretic particles 602 in the microchannels 35~37 by assembly of the dielectrophoretic particles 602. Hence, when target DNAs (not shown in FIGS.) are provided by the continuous fluid, the contact probability between the target DNAs and the dielectrophoretic particles 602 can be highly promoted in the circumstance of high surface area to volume ratio.

In addition, the electric field intensity of the narrow ends 382 of the V-shaped trapping electrodes 38 is about four times higher than that of two outward extension ends resulting from the gathering of the electric field lines. Moreover, the size of the gaps between the dielectrophoretic particles 602 of the particle assembly 600 close to the narrow ends 382 is only about 10~20 nm. Consequently, the intensity of the electric field in the nano gaps close to the narrow ends 382 can be enhanced more than 100 times higher. For example, if the AC voltage applied on the V-shaped trapping electrodes 38 is 17 Vpp and its frequency is 1 MHz, the intensity of the electric field in the nano gaps can be enhanced about 100 times that of the original electric filed and reached about $10^9$ V/m estimated by finite element analysis. Such electric field intensity is high enough to generate the dielectrophoretic force for effectively manipulating nanoscale molecules such as DNAs.

In the present embodiment, the aforementioned high electric field intensity can generate a strong positive dielectrophoretic force on the target DNAs moved through the particle assembly 600 by the continuous fluid and thereby attract the target DNAs into the gaps of the particle assembly 600. It promotes the contact probability between the target DNAs and the DNA probes on the surface of the dielectrophoretic particles 602 and thereby increases the hybridization rate of DNA.

Referring to FIG. 1 and FIGS. 5~7, however, the hybridization rate is also related to the electrostatic repulsive force between the target DNAs 700 and the DNA probes on the surfaces of the dielectrophoretic particles 602 (not shown in FIGS.). If the generated positive dielectrophoretic force is much lower than the electrostatic repulsive force between the target DNAs 700 and the dielectrophoretic particles (shown in FIG. 5), it is difficult for the target DNAs 700 to contact with the DNA probes on the surface of the dielectrophoretic particles 602. In contrast, most of the target DNAs 700 is taken away from the particle assembly 600 by the hydrodynamic force provided by the continuous fluid 800 and thereby the hybridization is inefficient.

On the contrary, if the adhesion force contributed by the positive dielectrophoretic force is much stronger than the electrostatic repulsive force between the target DNAs 700 and the dielectrophoretic particles 602 (shown in FIG. 6), the hybridization reaction can occurs between the target DNAs 700 and the DNA probes in the particle assembly 600 close to the periphery of the outer edges of the two extension ends of the V-shaped trapping electrodes 38 immediately.

However, when the adhesion force generated by the positive dielectrophoretic force is adjusted to be little higher than the electrostatic repulsive force between the target DNAs 700 and the dielectrophoretic particles 602 (shown in FIG. 7), the target DNAs can be moved along the particle assembly 600 at the periphery of the V-shaped trapping electrodes 38 and toward the region with the highest intensity of the electric field of the particle assembly 600 (i.e. toward the tip 601 of the particle assembly 601) by the interaction of the positive dielectrophoretic force and the hydrodynamic force provided by the continuous fluid 800 with the predetermined flow rate. It is because the electric field of the aforementioned region can generate a stronger positive dielectrophoretic force on the target DNAs 700 such that the target DNAs 700 can be con- Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

centrated at the tip 601 of the particle assembly 600. The related experiment results are illustrated later.

Figure 8:
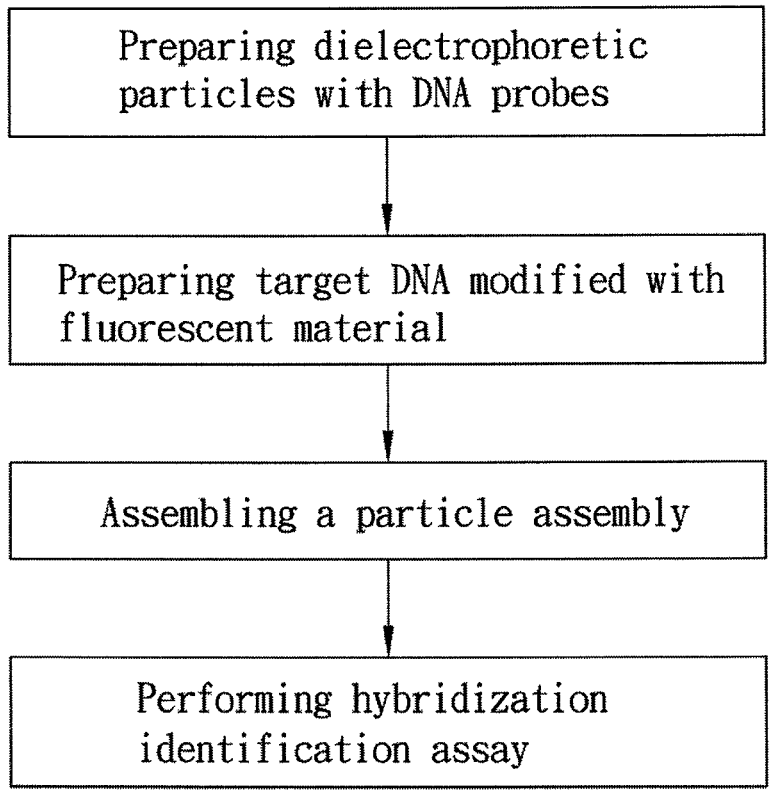
FIG. 8 is a flow chart in accordance with the first preferred embodiment.

As shown in FIG. 8, the method of microbial identification by a dielectrophoretic force in accordance with the present invention includes the steps described in the following.

The first step is to prepare dielectrophoretic particles with DNA probes. According to the species of the target microbes, DNA probes with specific sequences are selected and then fixed on the surface of a predetermined nanoscale dielectrophoretic particle by modification.

In the present embodiment, the microbes taken for exemplary description are those within Candida causing major infection in clinical practice such as Candida tropicalis (purchased from BCRC; Deposit No. 20521) and Candida albican (purchased from BCRC; Deposit No. 2051). The data of DNA probes corresponding to the aforementioned microbes are listed in Table 1. The diameter of the aforementioned dielectrophoretic particles is 500 nm and the surface of the dielectrophoretic particles is made of silica and modified with COOH functional groups. Before the modification of the DNA probes, EDC is used as an activation initiator between the COOH group and NHS. Then, NHS is added to modify $CONH_2$ groups on the surface of the dielectrophoretic particles. The DNA probes complementary to the target DNAs are used in the concentration range of nM and fixed tightly on the dielectrophoretic particles. The production of the DNA probes and the modification of the DNA probes on the dielectrophoretic particles are well-known in the field of the present invention and thereby need no further description. In the present embodiment, the surface of each of the dielectrophoretic particles is modified with for example but not limited to about 50 DNA probes.

For description, the DNA probes corresponding to Candida tropicalis are described as the first DNA probes and the dielectrophoretic particles modified with the first DNA probes are described as the first dielectrophoretic particles. The DNA probes corresponding to Candida albican are described as the second DNA probes and the dielectrophoretic particles modified with the second DNA probes are described as the second dielectrophoretic particles.

Considering that the production of the target DNA modified with fluorescent material is well-known in the field of the present invention and not the technical feature of the present invention, there is no need to go into further details. In addition, the type of the fluorescent material used herein is not limited to the aforementioned and the fluorescent material can be replaced with color display material as well.

Figure 9:
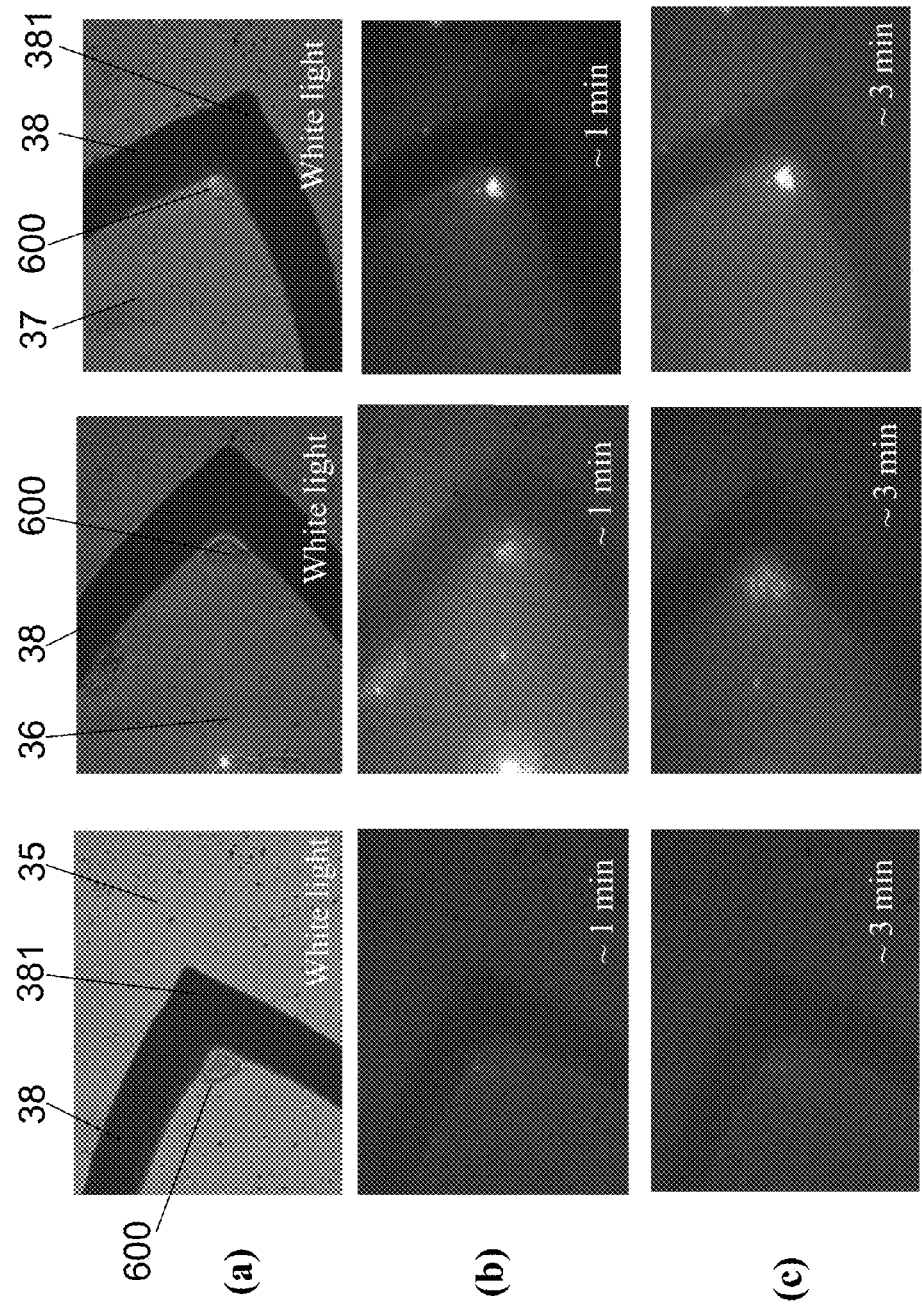
FIG. 9 is the image showing the detected time-varied fluorescence of different DNA probes in accordance with the first preferred embodiment.

Then, the particle assembly 600 is assembled. Referring to FIGS. 1 and 9(a), the first and second dielectrophoretic particles are well mixed in a specific fluid independently. In the present embodiment, the specific fluid is made by diluting 1×PBS (Phosphate Buffered Saline) 15 fold with distilled water and has the electrical conductivity of 1 mS/cm. Two fluids are injected into the first injection channel 31 and the third injection channel 33 of the dielectrophoretic microfluidic chip respectively and then flow into the main channel 34 for forming particle flows. The flow rate of the particle flows is maintained at 1 μl/min so as to the particle flows can flow into the microchannels 35~37 as laminar flows respectively, The fluid flowing into the first microchannel 35 contains only the first dielectrophoretic particles, the fluid flowing into the third microchannel 37 contains only the second dielectrophoretic particles and the fluid flowing into the second microchannel 36 contains both of the first and second dielectrophoretic particles.

Meanwhile, an AC at a frequency of 10 MHz and a voltage of 20 Vpp is applied to the V-shaped trapping electrodes 38 symmetrically disposed on the top side and the bottom side of the microchannels 35~37 to generate negative dielectrophoretic forces on the first and the second dielectrophoretic particles in the fluid.

Since the dielectrophoretic forces are generated on the dielectrophoretic particles, the dielectrophoretic particles gradually gather and assemble into the particle assembly 600 at the narrow end 382 of the V-shaped trapping electrodes 38 by the interaction of the hydrodynamic force provided by the continuous fluid and the negative dielectrophoretic force. In other words, the particle assembly 600 is assembled at the region with the highest electric field intensity close to the V-shaped trapping electrodes 38. In the present embodiment,

TABLE 1

| microbes | DNA probes (5'~3') | length | site |
|---|---|---|---|
| C. albican (BCRC 20511) | Ttatcaacttgtcacaccagattattact (SEQ ID NO: 1) | 29 | 102-130(1) |
| C. tropicalis (BCRC 20521) | actcattttaagcgacttag (SEQ ID NO: 2) | 20 | 69-88(2) |

(1) is ITS1;
(2) is ITS2

After that, target DNAs modified with fluorescent material are prepared. The target DNAs used in the present embodiment are from Candida albican (BCRC 20511) and is capable of hybridizing with the second DNA probes modified on the second dielectrophoretic particles. The target DNAs are amplified by asymmetric PCR (ITS1:ITS4=100:1). Since there is a great difference in concentration between two primers y complementary to different ends of the target DNAs respectivel, a plenty of single strain DNAs (ssDNA) is present in the amplified product. The primers are labeled with FITC fluorescence at the 5' ends such that the amplified DNA product is fluorescent and capable to be applied in fluorescent assay for hybridizing with the DNA probes. Additionally, the target DNAs is about 500 bases in length.

the number of the dielectrophoretic particles in the particle assembly 600 is $2 \times 10^4$ and the size of the gaps between the dielectrophoretic particles is about 10~20 nm.

After that, the hybridization identification assay is performed. After the particle assembly 600 is completely assembled, the fluids containing the dielectrophoretic particles are not injected further. Then, the fluid containing the target DNAs is injected into the second injection channel 32 and flows into the main channel 34. The fluid containing the target DNAs continuously flows into the microchannels 35~37 at a predetermined flow rate. In the present embodiment, the concentration of target DNA is 100 pM, the flow rate is 1 μl/min and the AC voltage applied to the V-shaped trapping electrodes 38 is reduced to 17 Vpp with the reduced frequency of 1 MHz.

When the target DNAs are moved into the microchannels 35~37 by the fluid and close to the particle assembly 600, the positive dielectrophoretic force can be generated on the target DNAs by the electric field of the intensity about $10^9$ V/m in the nano gaps. In addition, the generated positive dielectrophoretic force is slightly stronger than the electrostatic repulsive force between the target DNAs and the surface of the dielectrophoretic particles.

Referring to FIGS. 9(b) and (c), since the second DNA probes of the second dielectrophoretic particles assembled in the third microchannel 37 is provided for C. albican (BCRC 20511) and the first DNA probes of the first dielectrophoretic particles assembled in the first microchannel 35 is provided for C. tropicalis, the target DNAs are attracted into the nano gaps of the particle assembly 600 when moved close to the particle assembly 600 in the third microchannel 37. In addition, because the highest intensity of the electric field is present at the tip 601 of the particle assembly 600, the target DNAs are concentrated at the tip 601 of the particle assembly 600 by the influence of the continuous fluid and the attraction of the positive dielectrophoretic force and then rapidly hybridize with the DNA probes. Because the hybridization occurs locally at a small spot of the particle assembly 600, a significant fluorescent response on the particle assembly 600 in the third microchannel 37 can be observed within one minute.

Since the target DNAs can not hybridize with the first DNA probes on the first dielectrophoretic particles, they are gradually taken away from the particle assembly 600 by the continuous fluid. In more detailed, it is because no hybridization occurs even though the target DNAs are indeed attracted into the particle assembly 600. Consequently, no fluorescent response is observed after 3 minutes. In contrast, both the first and the second dielectrophoretic particles are present in the second microchannel 36 and the target DNAs can hybridize with the second DNA probes on the second dielectrophoretic particles of the particle assembly 600 such that little fluorescent response can be observed at the tip 601 of the particle assembly 600 but the luminance of the fluorescent response in the image of the second microchannel 36 is much lower than that in the image of the third microchannel 37.

Figure 10:
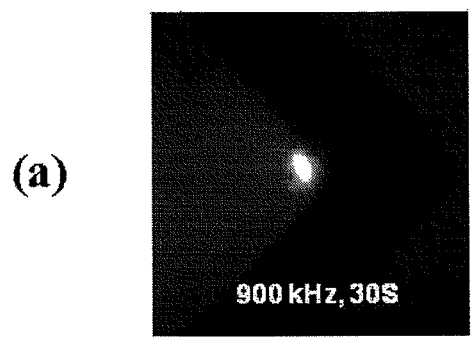
FIG. 10 is the fluorescent image showing the particle assembly in different positive dielectrophoretic forces in accordance with the first preferred embodiment.
Figure 10:
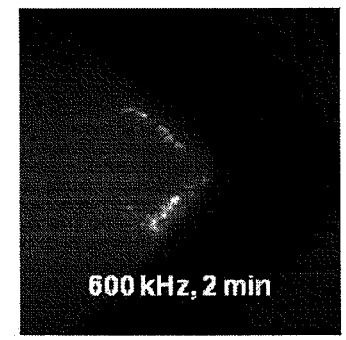
Figure 10:
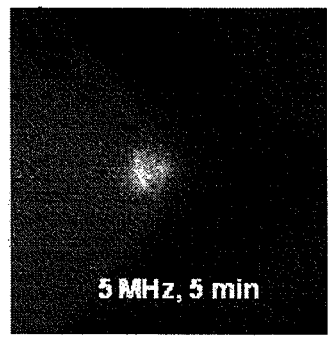

As shown in FIG. 10, the influence of the positive dielectrophoretic force on the target DNAs and the electrostatic repulsive force between the target DNAs and the DNA probes on the surface of the dielectrophoretic particles on the rate of the hybridization is further described hereunder. The dielectrophoretic particles used in the present embodiment are glass beads with a diameter of 500 nm, and the target DNAs are obtained from a green crab (Carcinus maenas) cells (Source: Department of Biological Sciences, University of Notre Dame Ind., USA). The DNA probes are designed corresponding to the target DNAs, and the sequences of the DNA probes are listed in Table 2. The strength of the positive dielectrophoretic force can be adjusted by changing the frequency of the AC voltage applied to the V-shaped trapping electrodes. The target DNAs are mixed in 0.08×PBS having an electrical conductivity of 1 mS/cm. The concentration of the target DNAs is 100 pM. The AC voltage applied to the V-shaped trapping electrodes is 17 Vpp and has frequencies of 600 kHz, 900 kHz and 5 MHz respectively. Additionally, as the fluorescence intensity reaches 8000±2000, it is recorded to represent that effective hybridization has been achieved.

TABLE 2

| Source of the target DNAs | DNA probe(5' to 3') | length |
|---|---|---|
| Green crab (Carcinus maenas) | ttagggattttctctttacattttgc (SEQ ID NO: 3) | 26 |

As shown in FIG. 10(a), when the positive dielectrophoretic force is slightly stronger than the electrostatic repulsive force between the target DNAs and the dielectrophoretic particles (at the frequency of AC voltage of 900 kHz), most of the hybridization occurs at the tip of the particle assembly. Hence, it just takes about 30 seconds to confirm a bright spot with predetermined fluorescence intensity at the tip of the particle assembly. As shown in FIG. 10(b), however, when the positive dielectrophoretic force is much stronger than the electrostatic repulsive force between the target DNAs and the dielectrophoretic particles (at the frequency of AC voltage of 600 kHz), most of the hybridization occurs around the particle assembly and thereby the region of hybridization is expanded. Consequently, the fluorescent response can not be observed until about 2 minutes later. As shown in FIG. 10(c), when the positive dielectrophoretic force is much weaker than the electrostatic repulsive force between the target DNAs and the dielectrophoretic particles (at the frequency of AC voltage of 5 MHz), only a small amount of the target DNAs hybridizes with the DNA probes even after 5 minutes. Particularly, according to the position of the weak fluorescence, the range of the hybridization is across the particle assembly and it is difficult to obtain sufficient certain fluorescence intensity for determining whether the effective hybridization has been achieved.

Figure 11:
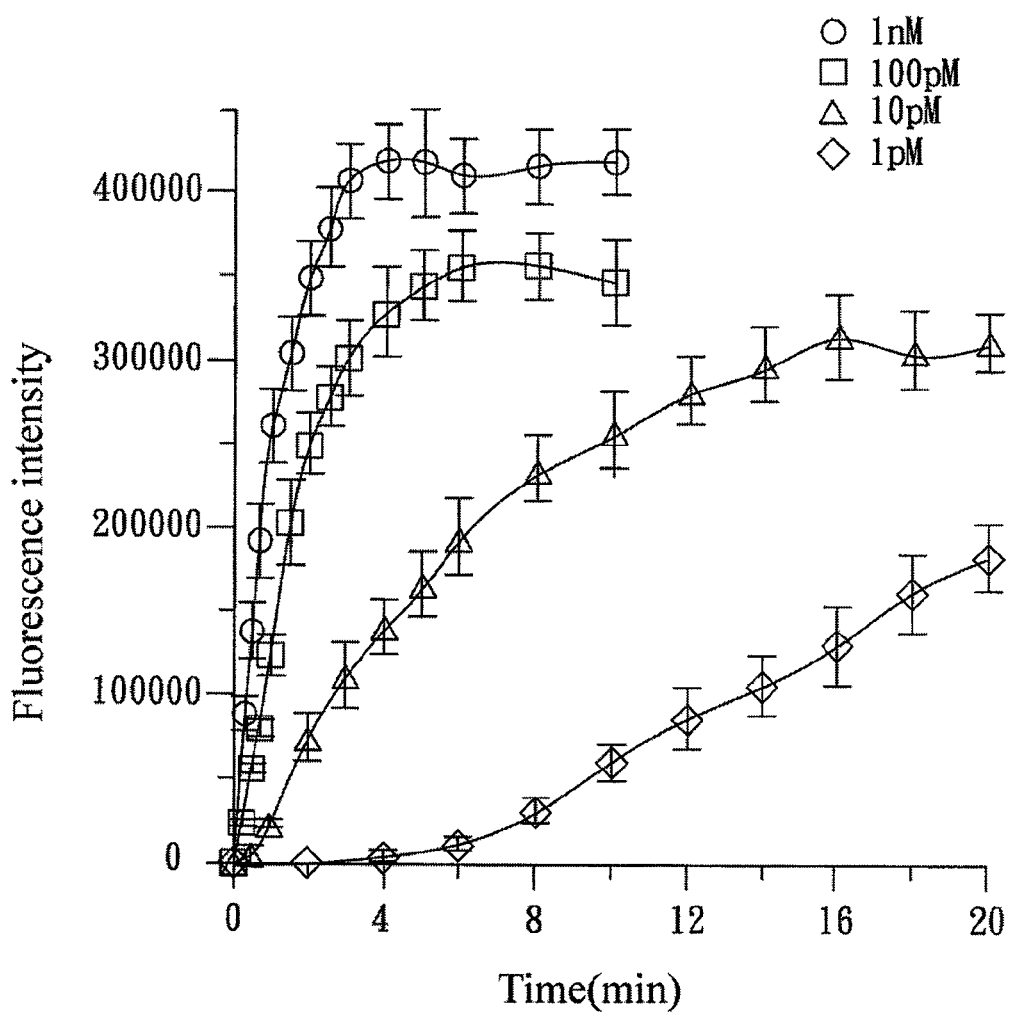
FIG. 11 is a diagram showing the detected time-varied fluorescence intensity of different DNA concentration in accordance with the first preferred embodiment.

As shown in FIG. 11, different concentration of the target DNAs obtained from the green crab (Carcinus maenas) are used to perform assays with the corresponding DNA probes for analyzing reaction time of hybridization and fluorescence intensity. Similarly, as the fluorescence intensity reaches 8000±2000, it is recorded to represent that effective hybridization has been achieved. As a result, it only takes about 30~40 seconds for 1 nM or 100 pM target DNAs and about 15 minutes for 1 pM target DNAs to achieve the expected fluorescence intensity. The assay time of each concentration is brief. Even though the target DNAs have a low concentration of 1 pM, the reaction period of the total assay is significantly reduced comparing to a traditional DNA array.

Figure 12:
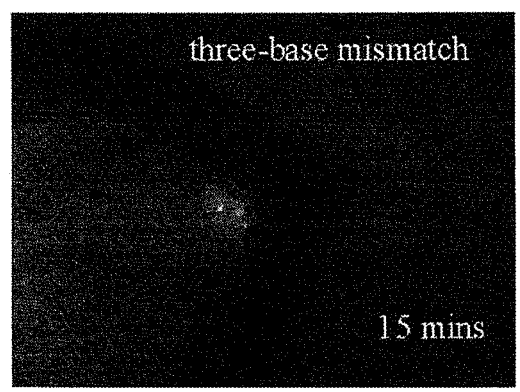
FIG. 12 is the fluorescent image showing the particle assembly modified by the DNA probes with three-base mismatch in hybridization in accordance with the first preferred embodiment.
Figure 13:
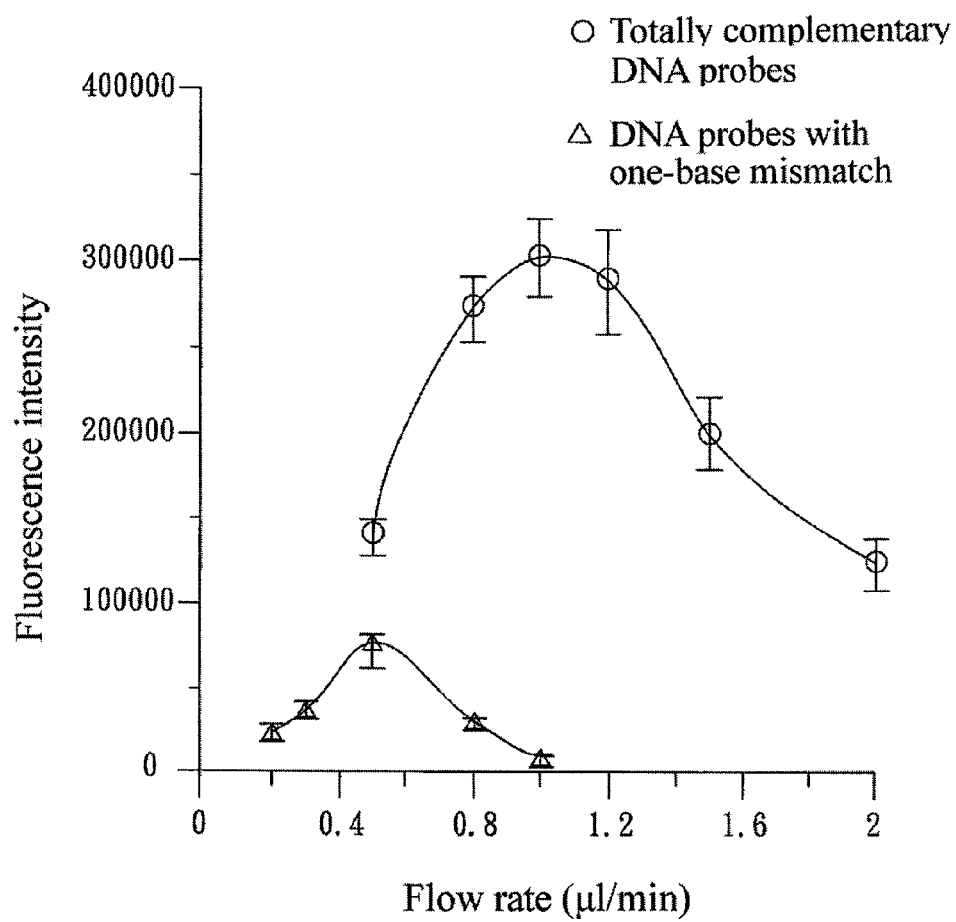
FIG. 13 is the variation diagram showing the relationship between the flow rate of the fluid and the fluorescence intensity during hybridization of the particle assembly modified by the DNA probes with one-base mismatch in accordance with the first preferred embodiment.

As shown in FIGS. 12 and 13, the DNA sequences of the DNA probes are modified to introduce one-base mismatch and three-base mismatch with the target DNAs for analyzing the specificity of the present invention. The sequences of the totally complementary DNA probes, the DNA probes with three-base mismatch and the DNA probes with one-base mismatch are as shown in Table 3. The sequence of totally complementary DNA probes is identical with the one listed in Table 2. The target DNAs used herein is the aforementioned target DNAs obtained from the green crab (Carcinus maenas). The concentration of the target DNAs is 100 pM. The AC voltage applied herein is 17 Vpp and has a frequency of 1 MHz.

TABLE 3

| | DNA probes (5' to 3') | | length |
|---|---|---|---|
| Totally complementary | ttagggattttctctttacattttgc | (SEQ ID NO: 3) | 26 |
| Three-base mismatch | ttagggattttctctttacatttacg | (SEQ ID NO: 4) | 26 |
| One-base mismatch | ttagggattttctctttacattttgg | (SEQ ID NO: 5) | 26 |

As the result shown in FIG. 12, after the target DNAs are moved in the fluid at the flow rate of 1 μl/min for hybridization with the DNA probes for 15 minutes, only a weak fluorescent response is present at the inside of the particle assembly modified with the DNA probes with three-base mismatch resulting from a small number of the target DNAs attracted by the positive dielectrophoretic force and remained inside the particle assembly.

Additionally, as the result shown in FIG. 13, when the flow rate of continuous fluid is lower than 0.8 μl/min, the target DNAs can still hybridize with the DNA probes with one-base mismatch such that fluorescent response with certain intensity can be observed on the particle assembly. However, when the flow rate of continuous fluid is raised to 0.8~1.2 μl/min, the target DNAs hybridized with DNA probes with one-base mismatch are flushed away by the flushing force of the continuous fluid. Hence, the fluorescence intensity observed on the particle assembly modified with the DNA probes with one-base mismatch is reduced significantly. The fact that the fluorescence intensity varying between the results of the totally complementary DNA probes and the DNA probes with one-base mismatch shows that the non-specific adherence between the DNA probes only with one-base mismatch and the target DNAs is fairly low in the continuous fluid at the specific flow rate. It is also because the continuous fluid at high shear rate in the microchannel can enhance the selectivity to achieve the abovementioned one-base mismatch discrimination. It demonstrates the excellent specificity of the present invention.

To sum up, it is proved that the combination of the hydrodynamic force provided by the continuous fluid, the particle assembly assembled by the dielectrophoretic particles and the positive dielectrophoretic force on the target DNAs generated by the high electric field intensity in the nano gaps of the particle assembly not only can increase the reaction rate and the sensitivity but also provides excellent specificity in hybridization. In the abovementioned embodiments, the target DNAs obtained from C. tropicalis, C. albican and the green crab are only taken for exemplary description and, therefore, the species of microbes, the types of cells and the sequences of the corresponding DNA probes in accordance with the present invention are not limited to the aforementioned. In addition, the present invention can be used for rapid identification of biomolecules, from which nucleic acids can be extracted, such as microbes, cells and virus.

While the dielectrophoretic particles are made from silica in the present embodiment, they can also be made from other insulating material in practice. Furthermore, the diameter of the dielectrophoretic particles can be adjusted in accordance with the requirement as long as the enhanced electric field in the gaps between the dielectrophoretic particles of the particle assembly is capable of generating the positive dielectrophoretic force on the target DNAs.

Figure 15:
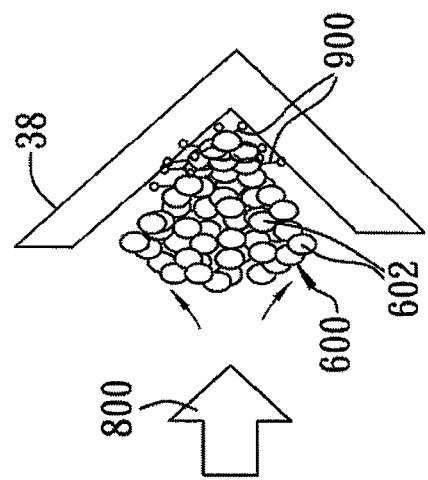
FIG. 15 is a similar figure of FIG. 14 showing the antibodies modified with fluorescent material binds to the particle assembly.
Figure 14:
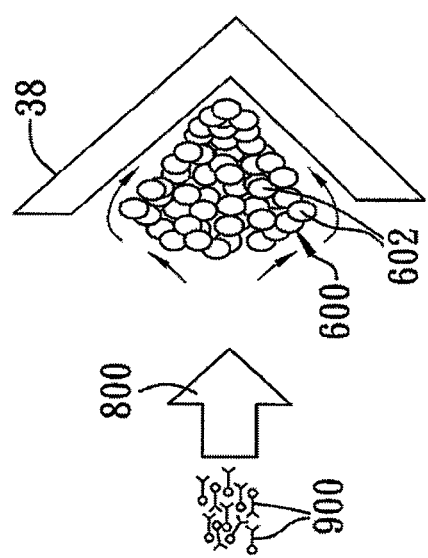
FIG. 14 is a schematic figure of the method of microbial identification in accordance with the second preferred embodiment of the present invention and shows the microbial-type dielectrophoretic particles are assembled to form the particle assembly.

As shown in FIGS. 14 and 15, the difference between the second preferred embodiment and the first embodiment is the type of the dielectrophoretic particles and the species contributing corresponding target DNA for identification.

In the first embodiment, the nano particles made from silica are used as the dielectrophoretic particles and the target manipulated by a dielectrophoretic force is DNAs in nanoscale structure. In the present embodiment, however, the dielectrophoretic particles 602 is the microbe itself and the target manipulated by the dielectrophoretic force is antibodies 900 modified with fluorescent material. In other words, the present embodiment described herein is for microbial identification by the antibody-antigen interaction between specific proteins on the surface of the microbe and the antibodies 900.

The microbe also has dielectrophoresis feature and, therefore, can be manipulated by a negative dielectrophoretic force generated by applying an AC with a predetermined voltage and a frequency to the V-shaped trapping electrodes 38. The microbes (with the diameter of 250 nm to 10 μm) used as the dielectrophoretic particles 602 in the continuous fluid are assembled to form a particle assembly 600 with nano gaps in front of the V-shaped trapping electrodes 38. After that, the high intensity of the electric field can be formed in the nano gaps to generate the negative dielectrophoretic force against the positive dielectrophoretic force on the antibodies 900.

In the present embodiment, since the size of antibodies 900 is larger than that of DNAs, the gaps between the microbial type dielectrophoretic particles 602 can be relatively widen to 50~100 nm with no influence of manipulating the antibodies 900 by the dielectrophoretic force effectively.

The present embodiment performs the method of microbial identification by immunoassay in accordance with the present embodiment includes the steps described in the following.

First, the particle assembly 600 is assembled. The dielectrophoretic particles 602 (i.e., the target microbes) are injected into a microchannel (not shown in the FIG.) of a dielectrophoretic microfluidic chip at a predetermined flow rate. An AC with a predetermined frequency and voltage is applied to the V-shaped trapping electrodes 38 of the microchannels. The microbial type dielectrophoretic particles 602 are blocked and assembled in front of the V-shaped trapping electrodes 38 and assembled into a particle assembly 600 by the hydrodynamic force provided by the continuous fluid.

After that, the identification by immunoassay is implemented. The specific antibodies 900 modified with fluorescent material and only interacting with specific microbes are added and mixed in a predetermined fluid. The predetermined fluid containing the antibodies 900 is injected into the microchannel at a predetermined flow rate. Meanwhile, the frequency and voltage of the AC applied to the V-shaped trapping electrodes 38 are adjusted to form the high electric field intensity in the gaps of the dielectrophoretic particles 602 of particle assembly 600 to generate the positive dielectrophoretic force for attraction of the antibodies 900. During the antibodies 900 pass through the particle assembly 600, they can be attracted into the particle assembly 600 by the positive dielectrophoretic force such that the contact probability between the antibodies 900 and the microbial type dielectrophoretic particles 602 can be highly increased.

When having antigen-antibody interaction with specific proteins on the surface of the microbial type dielectrophoretic particles 602, the antibodies 900 can be gradually bonded to and fixed on the dielectrophoretic particles 602. Consequently, a significant fluorescent response can be detected on the particle assembly 600. On the contrary, when the antibodies 900 has no specific antigen-antibody interaction with the dielectrophoretic particles 602, the antibodies 900 are gradually removed from the particle assembly 600 by the hydrodynamic force provided by the continuous fluid and thereby no fluorescent response can be detected on the particle assembly 600. Similarly, rapid strain identification can be practiced in the same way. In addition, the interaction between the antibodies 900 and the microbes has very high specificity, and all of the interaction between the antibodies 900 and the microbial type dielectrophoretic particles 602 occurs intensively at a small region in front of the V-shaped trapping electrodes 38. Accordingly, the method in accordance with the present embodiment is featured with higher sensitivity and faster reaction rate comparing to traditional ELISA. Furthermore, by the aforementioned assembly process, the method in accordance with the present invention can also be applied in microbe sample in a low concentration.

In summary, the method in accordance with the present invention is to form a particle assembly with nano gaps by assembling dielectrophoretic particles by a hydrodynamic force provided by a continuous fluid and a negative dielectrophoretic force. Hence, a high electric field for generating a dielectrophoretic force to efficiently manipulate nanoscale biomolecules can be directly formed in the nano gaps between the dielectrophoretic particles instead of being provided with nanosize trapping electrodes manufactured in nanoprocess. It breaks the bottleneck of the manipulation of nanoscale molecules (such as DNAs, antibodies, proteins etc.) by dielectrophoretic forces.

In addition, whether the method used to generate the positive dielectrophoretic force on the target DNA in the continuous fluid by modifying the surface of the aforementioned dielectrophoretic particles of the particle assembly with the DNA probes and usage of a high electric field intensity in the nano gaps of the particle assembly or the method used to generate the positive dielectrophoretic force on the antibodies in the continuous fluid by directly assembling the target microbes to form the aforementioned particle assembly and usage of a high electric field intensity in the nano gaps between the microbes is implemented by continuous injection instead of diffusion mechanism used in a tank reactor. Hence, the reaction rate can be increased and a significant fluorescent response can be observed in several minutes. In addition, most of the non-specific adherence can be flushed away by the fluid. The target DNA and the antibody in a low concentration can be further concentrated on the particle assembly by the continuous fluid. Briefly, with the proper flow rate of the continuous fluid and electric field frequency, the target DNAs or the antibodies can be intensively concentrated in a small region resulting in significant increase in the sensitivity of fluorescent assay. Comparing to the concentration issue of the target DNA (about 1~10 nM) for the conventional DNA array, the limit of the methods in accordance with the present invention is about $10^4$~$10^5$ times lower than that of the conventional DNA array. That is, the concentration of the target DNAs can be down to 1 pM. The results of the target DNAs in different concentrations of 100 pM and 1 pM can be observed in 1 and 15 minutes respectively.

Since the positive dielectrophoretic force can be used against the electrostatic repulsive force between the target DNAs and the DNA probes, the method in accordance with the present invention can be applied for hybridization in the fluid with a lower ion concentration to prevent non-specific adhesion. Therefore, there is no need to heat up to melting temperature in hybridization. By the flushing force provided by the continuous fluid and the influence of the electric field, DNA sequences containing one-base mismatch can be discriminated from the others. It indicates an application filed for the methods in accordance with the present invention in primer design by using certain mechanism with high selectivity to discriminate different targets containing similar sequences. Therefore, the purpose of the present invention has been achieved.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A method of microbial identification applied with an dielectrophoretic microfluidic chip, wherein the dielectrophoretic microfluidic chip includes a first injection channels, a second injection channel, a third injection channel, a main channel extending horizontally and conducting to the injection channels at one end, and a first microchannel, a second microchannel and a third microchannel conducting to the right end of the main channel respectively, the method comprising the steps of:

injecting a continuous fluid containing first dielectrophoretic particles modified with first DNA probes into the first injection channel and a continuous fluid containing second dielectrophoretic particles modified with second DNA probes of a target microbe into the third injection channel respectively;

forcing the fluid containing first dielectrophoretic particles and the fluid containing second dielectrophoretic particles to flow through the main channel to the microchannels as laminar flows, the fluid flowing into the first microchannel contains only the first dielectrophoretic particles, the fluid flowing into the third microchannel contains only the second dielectrophoretic particles and the fluid flowing into the second microchannel contains both of the first and second dielectrophoretic particles;

assembling first dielectrophoretic particles individually, first dielectrophoretic particles will the second dielectrophoretic particles, and second dielectrophoretic particles individually on a surface thereof in the continuous fluid at a predetermined region in the first microchannel, the second microchannel and the third microchannel to form a particle assembly by a negative dielectrophoretic force and a hydrodynamic force provided by the continuous fluid, respectively;

narrowing gaps among the first dielectrophoretic particles, gaps among the second dielectrophoretic particles, and gaps among the first dielectrophoretic particles and the second dielectrophoretic particles of each of the particle assemblies to enhance the electric field in the gaps among the first dielectrophoretic particles, the gaps among the second dielectrophoretic particles, and the gaps among the first dielectrophoretic particles and the second dielectrophoretic particles;

injecting a fluid containing target DNAs of the target microbe into the second injection channel and flows into the main channel and the first microchannel, the second microchannel, and the third microchannel at a predetermined flow rate to move the target DNAs toward each of the particle assemblies; and generating a positive dielectrophoretic force by the enhanced electric field to attract the target DNAs toward the second dielectrophoretic particles of the particle assembly for hybridization with the second DNA probes, wherein the target DNAs are modified with fluorescent material or color display material, wherein six trapping electrodes with openings toward the continuous fluid are separately disposed on a top side and a bottom side of the first microchannel, the second microchannel, and the third microchannel with respect to each other.

2. The method in accordance with claim 1, wherein the positive dielectrophoretic force on the target DNAs is stronger than an electrostatic repulsive force between the second DNA probes and the target DNAs.

3. The method in accordance with claim 2, wherein each of the particle assemblies is assembled between the openings close to narrow ends of the trapping electrodes disposed on one of the microchannels by a negative dielectrophoretic force on the first dielectrophoretic particles and the second dielectrophoretic particles and has a tip with the highest electric field intensity close to the narrow ends of the trapping electrodes disposed on one of the microchannels, and the target DNAs are moved to and concentrated at the tip each of the particle assemblies for hybridization by the hydrodynamic force provided by the continuous fluid and the positive dielectrophoretic force simultaneously under adjustment of the relative ratio of the positive dielectrophoretic force on the target DNAs and the electrostatic repulsive force between the second DNA probes and the target DNAs.

4. The method in accordance with claim 2, wherein the diameter of the first dielectrophoretic particles and the second dielectrophoretic particles is from 100 to 2,000 nm and the size of the gaps among the first dielectrophoretic particles, gaps among the second dielectrophoretic particles, and gaps among the first dielectrophoretic particles and the second dielectrophoretic particles of each of the particle assemblies are from 10 to 20 nm.

5. The method in accordance with claim 4, wherein each of the particle assemblies is assembled between the openings close to narrow ends of the trapping electrodes disposed on the first microchannel, the second microchannel, and the third microchannel by a negative dielectrophoretic force on the first dielectrophoretic particles and the second dielectrophoretic particles and has a tip with the highest electric field intensity close to the narrow ends of the trapping electrodes disposed on the first microchannel, the second microchannel, and the third microchannel, and the target DNAs are moved to and concentrated at the tip of each of the particle assemblies for hybridization by the hydrodynamic force provided by the continuous fluid and the positive dielectrophoretic force simultaneously under adjustment of the relative ratio of the positive dielectrophoretic force on the target DNAs and the electrostatic repulsive force between the second DNA probes and the target DNAs.

6. A method of manipulation of nanoscale biomolecules applied with an dielectrophoretic microfluidic chip, wherein the dielectrophoretic microfluidic chip includes a first injection channels, a second injection channel, a third injection channel, a main channel extending horizontally and conducting to the injection channels at one end, and a first microchannel, a second microchannel and a third microchannel conducting to the right end of the main channel respectively, the method comprising the steps of:
    injecting a continuous fluid containing first dielectrophoretic particles modified with first DNA probes into the first injection channel and a continuous fluid containing second dielectrophoretic particles modified with second DNA probes of a target microbe into the third injection channel respectively;
    forcing the fluid containing first dielectrophoretic particles and the fluid containing second dielectrophoretic particles to flow through the main channel to the microchannels as laminar flows, the fluid flowing into the first microchannel contains only the first dielectrophoretic particles, the fluid flowing into the third microchannel contains only the second dielectrophoretic particles and the fluid flowing into the second microchannel contains both of the first and second dielectrophoretic particles;
    assembling first dielectrophoretic particles individually, first dielectrophoretic particles with the second dielectrophoretic particles, and second dielectrophoretic particles individually in the continuous fluid at a predetermined region in the first microchannel, the second microchannel and the third microchannel to form a porous particle assembly by a negative dielectrophoretic force and a hydrodynamic force provided by the continuous fluid, respectively;
    narrowing gaps among the first dielectrophoretic particles, gaps among the second dielectrophoretic particles, and gaps among the first dielectrophoretic particles and the second dielectrophoretic particles of each of the porous particle assemblies to enhance the electric field in the gaps among the first dielectrophoretic particles, the gaps among the second dielectrophoretic particles, and the gaps among the first dielectrophoretic particles and the second dielectrophoretic particles;
    injecting a fluid containing the nanoscale biomolecules into the second injection channel and flows into the main channel and the first microchannel, the second microchannel, and the third microchannel at a predetermined flow rate to move the nanoscale biomolecules toward each of the porous particle assemblies; and
    generating a positive dielectrophoretic force on the nanoscale biomolecules in the continuous fluid by the enhanced electric field in the gaps of the first dielectrophoretic particles and the second dielectrophoretic particles of each of the porous particle assemblies,
    wherein six trapping electrodes with openings toward the continuous fluid are separately disposed on a top side and a bottom side of the first microchannel, the second microchannel, and the third microchannel with respect to each other.

7. The method in accordance with claim 6, wherein the first dielectrophoretic particles and the dielectrophoretic particles are selected from non-biological particles or biological particles.

8. The method in accordance with claim 6, wherein the diameter of the first dielectrophoretic particles and the dielectrophoretic particles are from 100 to 2,000 nm and the size of the gaps among the first dielectrophoretic particles, the gaps among the second dielectrophoretic particles, and the gaps among the first dielectrophoretic particles and the dielectrophoretic particles of each of the porous particle assemblies is from 10 to 200 nm.

9. The method in accordance with claim 8, wherein the first dielectrophoretic particles and the dielectrophoretic particles are selected from non-biological particles or biological particles.

10. The method in accordance with claim 9, wherein the biological particles are microbes or cells.

11. The method in accordance with claim 9, wherein the non-biological particles are made of insulating material.

* * * * *

SEQUENCE LISTING

<160> NUMBER OF SEQ ID NOS: 5

<210> SEQ ID NO 1
<211> LENGTH: 29
<212> TYPE: DNA
<213> ORGANISM: Artificial sequence
<220> FEATURE:
<223> OTHER INFORMATION: Testing probe

<400> SEQUENCE: 1
ttatcaactt gtcacaccag attattact                29

<210> SEQ ID NO 2
<211> LENGTH: 26
<212> TYPE: DNA
<213> ORGANISM: Artificial sequence
<220> FEATURE:
<223> OTHER INFORMATION: Testing probe -continued

```
<400> SEQUENCE: 2
ttagggattt tctctttaca ttttgc                                              26

<210> SEQ ID NO 3
<211> LENGTH: 26
<212> TYPE: DNA
<213> ORGANISM: Artificial sequence
<220> FEATURE:
<223> OTHER INFORMATION: Testing probe

<400> SEQUENCE: 3
ttagggattt tctctttaca ttttgc                                              26

<210> SEQ ID NO 4
<211> LENGTH: 26
<212> TYPE: DNA
<213> ORGANISM: Artificial sequence
<220> FEATURE:
<223> OTHER INFORMATION: Testing probe

<400> SEQUENCE: 4
ttagggattt tctctttaca tttacg                                              26

<210> SEQ ID NO 5
<211> LENGTH: 26
<212> TYPE: DNA
<213> ORGANISM: Artificial sequence
<220> FEATURE:
<223> OTHER INFORMATION: Testing probe

<400> SEQUENCE: 5
ttagggattt tctctttaca ttttgg                                              26
```